(12) United States Patent
Kaufman et al.

(10) Patent No.: US 6,568,000 B1
(45) Date of Patent: May 27, 2003

(54) BATH APPARATUS WITH THERAPY CENTERS

(75) Inventors: Alon D. Kaufman, West Bloomfield, MI (US); Alex Wong Chi To, Sheung Shui (HK)

(73) Assignee: HoMedics, Inc., Commerce Township, MI (US)

( * ) Notice: Subject to any disclaimer, the term of this patent is extended or adjusted under 35 U.S.C. 154(b) by 0 days.

(21) Appl. No.: 10/126,246

(22) Filed: Apr. 19, 2002

(51) Int. Cl.[7] ............................................. A47K 3/022
(52) U.S. Cl. ........................... 4/622; 4/541.5; 601/22; 601/158
(58) Field of Search ................... 4/541.1, 541.5, 4/621, 622; 601/22, 67, 69, 70, 112, 113, 114, 158

(56) References Cited

U.S. PATENT DOCUMENTS

| | | |
|---|---|---|
| 5,029 A | 3/1847 | Thatcher |
| 1,775,942 A | 9/1930 | Millmather |
| 2,633,846 A | 4/1953 | Wray |
| 2,736,038 A | 2/1956 | Mansfield |
| 2,904,037 A | 9/1959 | Cassidy |
| 3,055,357 A | 9/1962 | Redka |
| 3,380,080 A | 4/1968 | Farrell |
| 3,467,969 A | 9/1969 | Szekely |
| 3,965,495 A | 6/1976 | McNair |
| 4,057,053 A | 11/1977 | Kunz |
| 4,184,488 A | 1/1980 | Bielich |
| 4,497,313 A | 2/1985 | Kurosawa |
| 4,513,735 A | 4/1985 | Friedson et al. |
| 4,569,337 A | 2/1986 | Baumann et al. |
| 4,620,529 A | 11/1986 | Kurosawa |
| 4,880,415 A | 11/1989 | Urakami |
| D330,426 S | 10/1992 | Elkerbout |
| D364,466 S | 11/1995 | Assmann et al. |
| 5,588,161 A | 12/1996 | Barradas |
| D390,963 S | 2/1998 | Scholpp |
| 5,729,841 A | 3/1998 | Chan |
| D405,535 S | 2/1999 | Schulz |
| D419,682 S | 1/2000 | Lie |
| 6,309,366 B1 | 10/2001 | Maxwell |

FOREIGN PATENT DOCUMENTS

| | | |
|---|---|---|
| DE | 1 429 756 | 2/1969 |
| DE | 29 45 866 A1 | 5/1981 |
| EP | 0 064 178 | 11/1982 |

OTHER PUBLICATIONS

Exhibit A—Remington Acupressure Foot Spa, Model F–7027 (Date unknown; believed to be prior art).
Exhibit B—Dr. Scholl's® Luxury Foot Spa, Model DR6655 (Date unknown; believed to be prior art).
Exhibit C—Dr. Scholl's® Infrared Luxury Foot Spa, Model DR6657 (Date unknown; believed to be prior art).
Exhibit D—Conair Ultra Massaging Foot Bath with Water Jet, Model FB12RD (Date unknown; believed to be prior art).

Primary Examiner—Robert M. Fetsuga
(74) Attorney, Agent, or Firm—Brooks & Kushman P.C.

(57) ABSTRACT

An apparatus is provided for bathing body parts, such as the feet. The apparatus includes a bath chamber for containing fluid, such as water, and receiving the body part therein. The bath chamber includes a bottom surface and a wall structure extending upwardly therefrom. A hood is attached to the wall structure and is arranged to at least partially cover the bath chamber, and a motor is mounted on an underside of the hood. At least two spaced therapy centers are disposed on the hood, where the therapy centers are operably connected to the motor for providing therapy to the body part when the body part is placed on one of the therapy centers.

38 Claims, 8 Drawing Sheets

BATH APPARATUS WITH THERAPY CENTERS

TECHNICAL FIELD

This invention relates to an apparatus for bathing body parts, such as the feet or hands, which includes therapy centers for providing therapy, such as massage, to the body parts.

BACKGROUND ART

Most people experience foot problems at some time in their lives. This is not surprising, considering that many people are employed in jobs that require them to be on their feet all day. In fact, even an average day of walking can exert force equal to several hundred tons of pressure on the feet.

In an attempt to alleviate a variety of podiatric problems, bathing of the feet has become a recognized therapeutic method. For example, soaking soothes the feet and aids in recovery from fatigue. Bathing of the feet also stimulates the circulation of blood therethrough, which results in increased metabolism and excretion. In addition, foot bathing facilitates the removal of painful growths such as calluses, bunions, and corns.

Many types of foot baths have been utilized as therapeutic devices for the feet. Typically, foot baths provide heated water for which the temperature is maintained via electrical means. In addition, current foot baths often provide massage to the feet through vibration of the foot bath. Vibratory massage enhances the therapeutic results achieved with soaking alone by further increasing circulation, as well as relaxing and massaging the muscles.

While heat and vibration applied to the feet in an overall manner is helpful, conventional foot baths are typically not designed with the capability to target specific areas of the feet. For example, it is common for a user to wish to concentrate treatment to a specific part or parts of his/her feet such as the ball, heel, or arch. Therefore, a need exists for a bath apparatus with the capability to focus therapy at specific locations of the body. Furthermore, it is advantageous to allow a user to accomplish targeted therapy of both feet simultaneously. Such a bath apparatus would not only allow users to tailor therapy regimens to their individual needs, but would also increase the speed at which therapy can be accomplished, thereby increasing the convenience for the user.

DISCLOSURE OF INVENTION

Therefore, it is an object according to the present invention to provide a bath apparatus for bathing body parts that is capable of providing targeted therapy, including massage, to the body parts.

It is a further object according to the present invention to provide a bath apparatus capable of providing targeted therapy to both feet at the same time.

Accordingly, an apparatus is provided for bathing body parts, such as the feet. The apparatus includes a bath chamber for containing fluid, such as water, and receiving the body part therein. The bath chamber includes a bottom surface and a wall structure extending upwardly therefrom. A hood is attached to the wall structure and is arranged to at least partially cover the bath chamber, and a motor is mounted on an underside of the hood. At least two spaced therapy centers are disposed on the hood, where the therapy centers are operably connected to the motor for providing therapy to the body part when the body part is placed on one of the therapy centers.

According to the present invention, the therapy centers are arranged to receive rotatable therapy attachments, such as attachments including raised nodes, a pumice stone, or a brush. A motor is mounted on an underside of the hood for imparting rotary motion to the therapy attachments via a gear train. Preferably, the gear train includes two outer gears each having a post affixed thereto, where the posts are accessible through a pair of openings in the hood. Each therapy attachment includes a projection extending outwardly therefrom, and the attachment projection and the gear post are arranged to securely engage such that the therapy attachments will rotate with the gear posts even when in contact with the body part. In a preferred embodiment, the hood includes a push-activated switch provided thereon, preferably operable via depression by a user's foot, for supplying power to the motor. The switch can be a multi-function switch which allows for multiple modes of activation of the therapy centers. Alternatively, motorized rotation of the therapy attachments can be activated by pressure of the body part on each therapy attachment.

In further accordance with the present invention, the hood is sloped upwardly at an angle of about 10 degrees from horizontal to provide for comfortable and ergonomic use of the therapy centers by the user. The hood also includes raised nodes provided thereon, and a slot formed therein sized to accommodate a user's hand to facilitate carrying of the bath apparatus. In addition, a storage unit is provided which is adapted to be attached to the wall structure for storing the therapy attachments therein.

In one embodiment, the wall structure includes a contact area having a heating member disposed thereon for providing heat to the body part when the body part is placed on the heating member. The bath chamber is preferably generally U-shaped and the contact area is generally peninsular and centrally disposed within the bath chamber, where the heating member is arranged to be uncovered by fluid contained in the bath chamber. In a preferred embodiment, the heating member uses infrared rays and includes raised nodes provided thereon.

The bath apparatus according to the present invention can further include a heater in communication with the bath chamber for maintaining the heat of the fluid contained therein, where the heater includes a rope heating element provided underneath the bottom surface of the bath chamber. In addition, an air pump and at least one bubble egress tube in communication with the pump and the bath chamber bottom surface are provided. The bubble egress tube includes a plurality of egress holes formed therein through which air from the pump is directed into the bath chamber in order to generate air bubbles in the fluid contained therein. Still further, the bath apparatus can include a vibration assembly in communication with the bath chamber for imparting vibration to the bath chamber.

According to another aspect of the present invention, a bath apparatus is provided having a bath chamber for containing water and receiving a user's feet therein. The bath chamber including a bottom surface and a wall structure extending upwardly therefrom. A hood attached to the wall structure is arranged to at least partially cover the bath chamber, and a motor is mounted on an underside of the hood. Spaced therapy centers are disposed on the hood and arranged to receive rotatable therapy attachments. The therapy centers are operably connected to the motor for imparting rotary motion to the therapy attachments such that, upon engagement by the feet, the therapy centers are capable of providing therapy to both feet simultaneously.

In accordance with yet another aspect of the present invention, a foot bath having multiple therapy centers is provided. The foot bath includes a bath chamber for containing a fluid and receiving at least one foot therein. The bath chamber includes a bottom surface and a wall structure extending upwardly therefrom, where the wall structure has a contact area. A hood is attached to the wall structure and is arranged to at least partially cover the bath chamber. A heat therapy center is disposed on the contact area for providing heat to the foot when the foot is placed on the heat therapy center, and spaced massage therapy centers are disposed on the hood for providing massage to the foot when the foot is placed on one of the massage therapy centers.

The above objects and other objects, features, and advantages of the present invention are readily apparent from the following detailed description of the best mode for carrying out the invention when taken in connection with the accompanying drawings.

BRIEF DESCRIPTION OF DRAWINGS

FIG. 8b is an internal view of the motor and gear system enclosed within the housing of FIG. 8a;

BEST MODE FOR CARRYING OUT THE INVENTION

Figure 1:
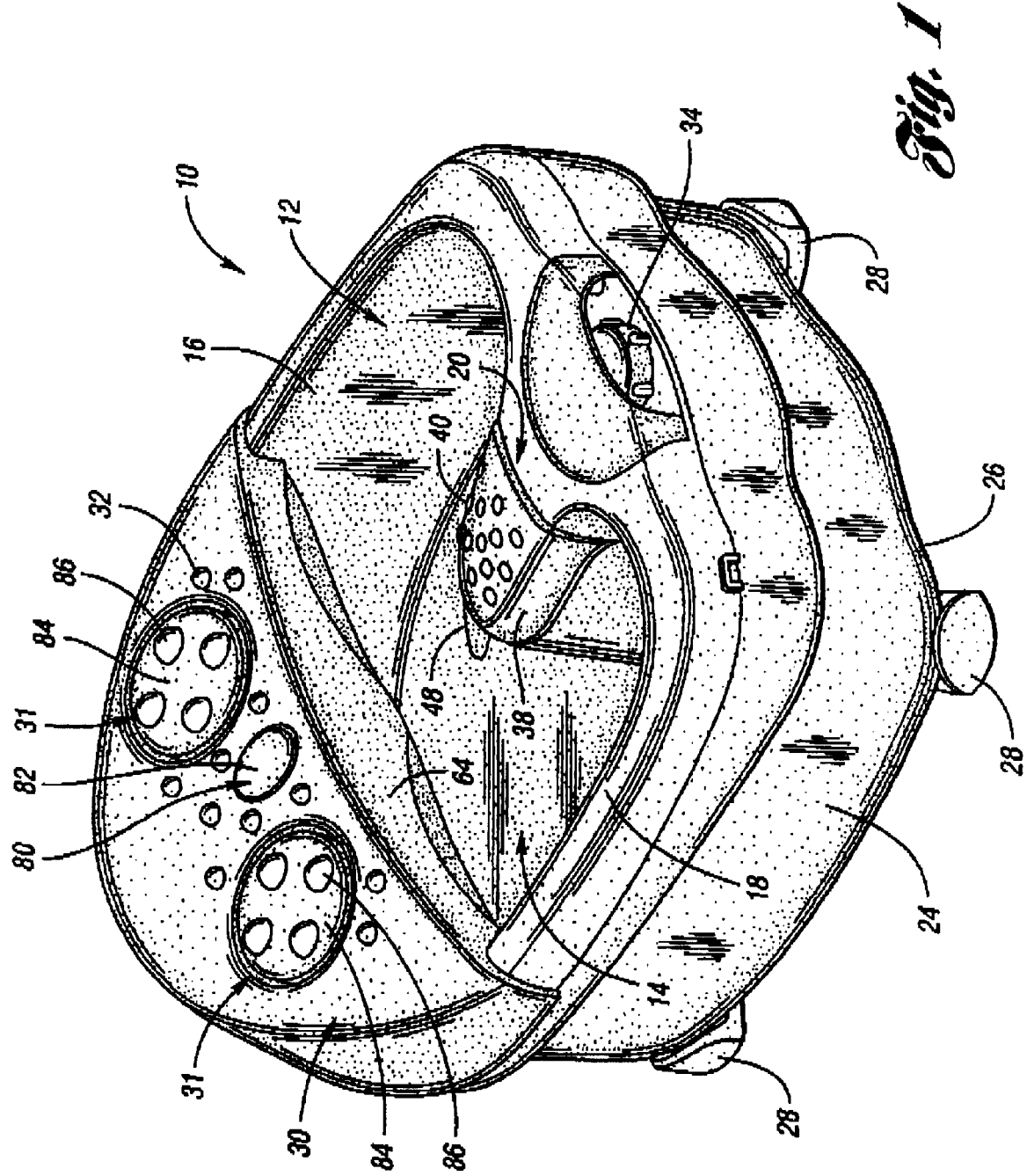
FIG. 1 is a perspective view of a bath apparatus constructed in accordance with the present invention.

Referring first to FIGS. 1–5, a bath apparatus constructed according to the present invention is depicted and designated generally by reference numeral 10. Bath apparatus 10 can be used to provide heat, bubbles, massage, and other therapy to body parts, such as the feet. Bath apparatus 10 is preferably constructed from a plastic material so as to be lightweight and portable, as well as durable, leakproof, and corrosion resistant. Although bath apparatus 10 is illustrated and described herein as being particularly adaptable for use as a foot bath, it is understood that bath apparatus 10 of the present invention may be used for bathing other body parts, such as the hands.

With reference to FIG. 1, bath apparatus 10 includes a bath chamber 12 for containing fluid, such as water, and receiving the body part, such as the foot, therein. Bath chamber 12 includes a floor or bottom surface 14 and a wall structure 16 extending upwardly therefrom. Wall structure 16 terminates in an upper surface 18 that includes a peninsular contact portion 20 adapted to be exposed when water is contained in bath chamber 12. Bottom surface 14 can be generally parallel to a supporting surface on which bath apparatus 10 is placed or, alternatively, bottom surface 14 could be slanted downwardly toward the user.

Figure 2:
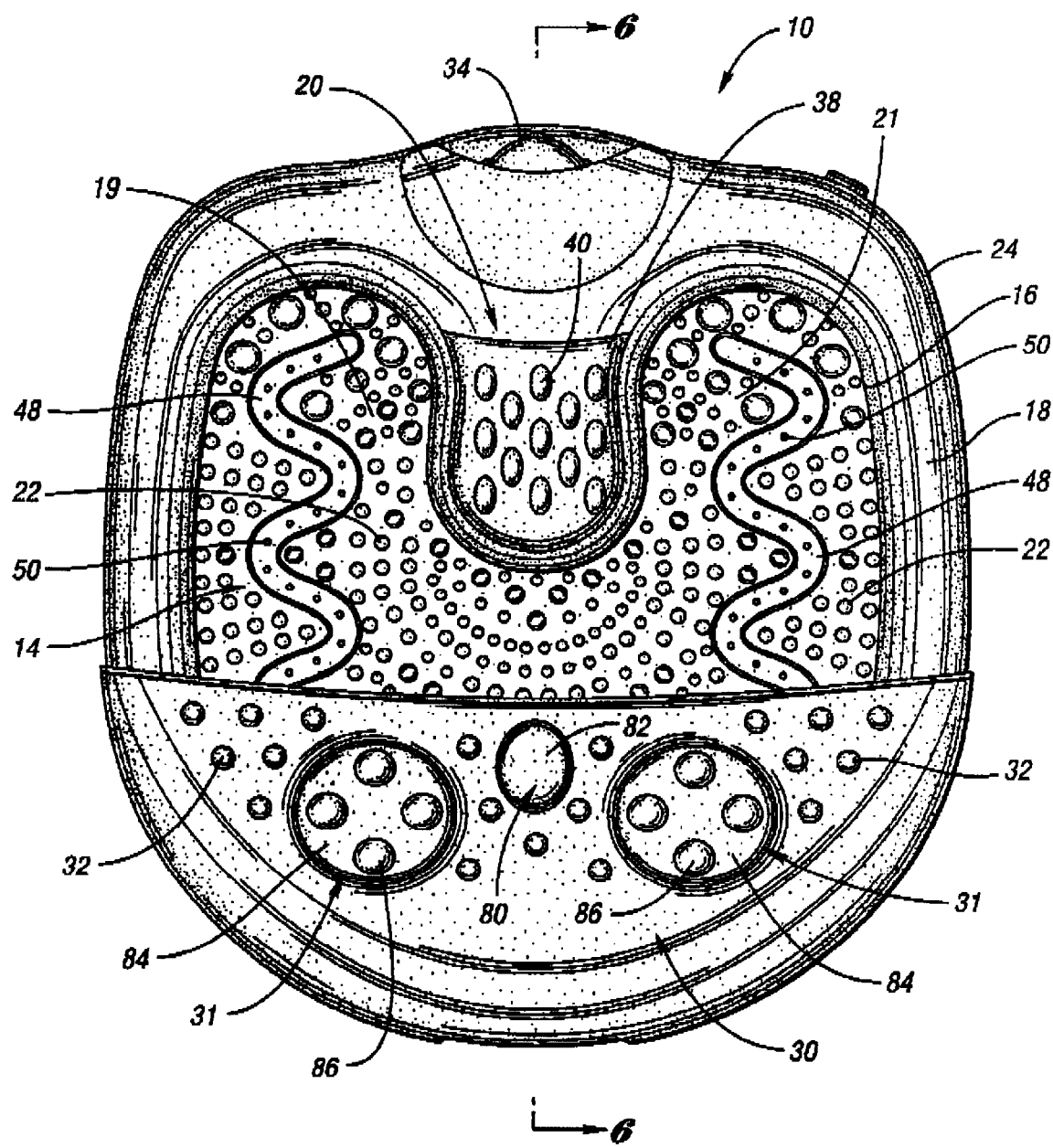
FIG. 2 is a top plan view of the bath apparatus of FIG. 1.

Bath chamber 12 is of a length and width to accommodate the feet of an adult user, such that sufficient space is provided to permit the user to readily insert and remove his/her feet and to allow each foot to be moved about slightly while in position within bath chamber 12. As shown in FIGS. 1 and 2, bath chamber 12 is generally U-shaped and contact portion 20 is centrally disposed within bath chamber 12. With this configuration, a user's feet are received on either side of peninsular contact portion 20, also denoted as first side 19 and second side 21 (see FIGS. 2 and 3) of bottom surface 14, wherein the feet are spaced apart sufficiently to provide comfortable placement.

Referring again to the top plan view of FIG. 2, bottom surface 14 of bath chamber 12 preferably includes a plurality of raised nodes 22 which can be of varying sizes. Nodes 22 function to massage the feet upon contact, and also allow water and heat to flow under the feet to improve blood circulation. Bottom surface 14 can also include detachable rollers (not shown) such that a user can glide his/her foot back and forth thereacross to help relieve tightness and tiredness along soles of feet, as well as for reflexology purposes.

Figure 3:
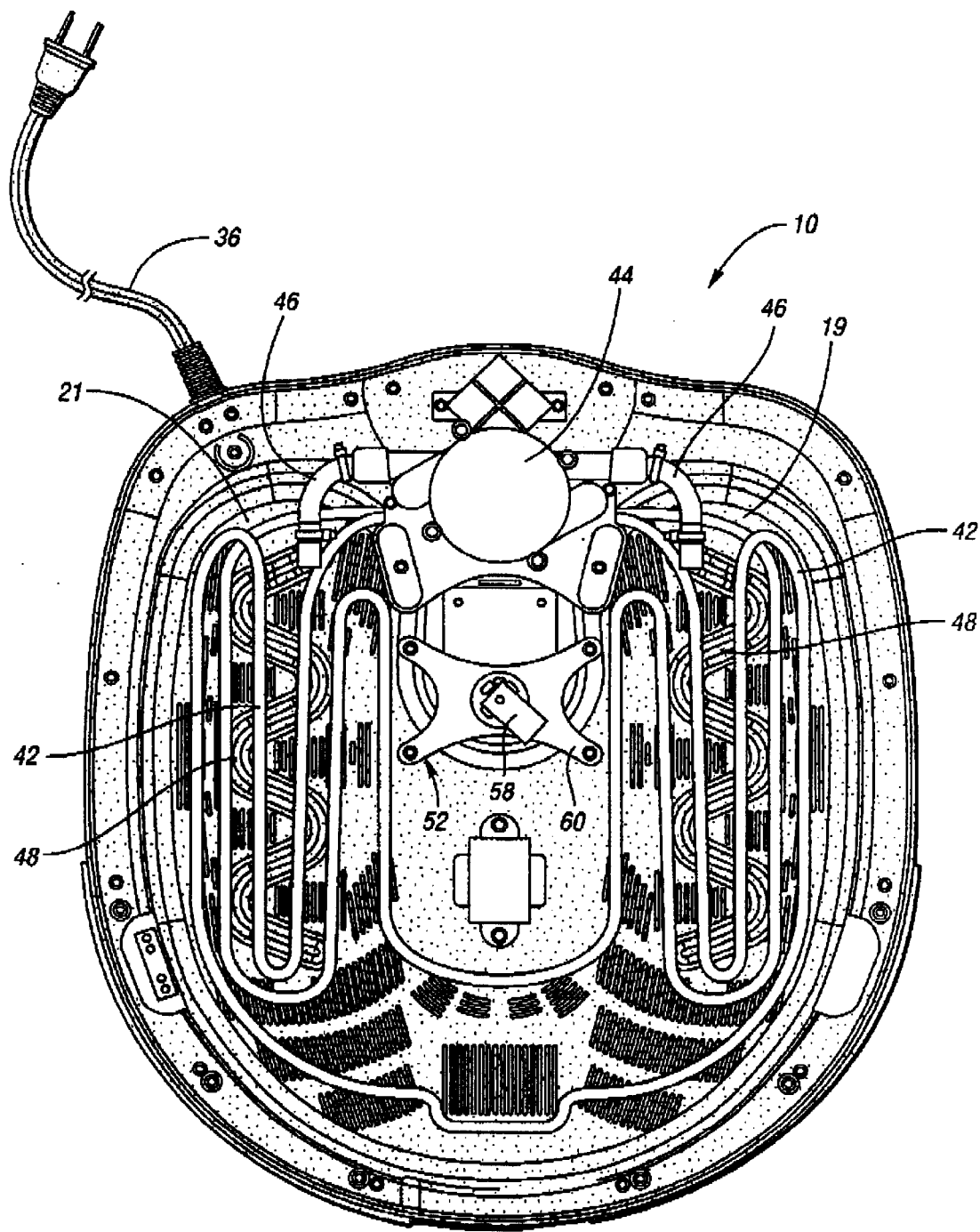
FIG. 3 is a fragmentary view of the pump, heating, and vibration assemblies located on the underside of the bath chamber.
Figure 4:
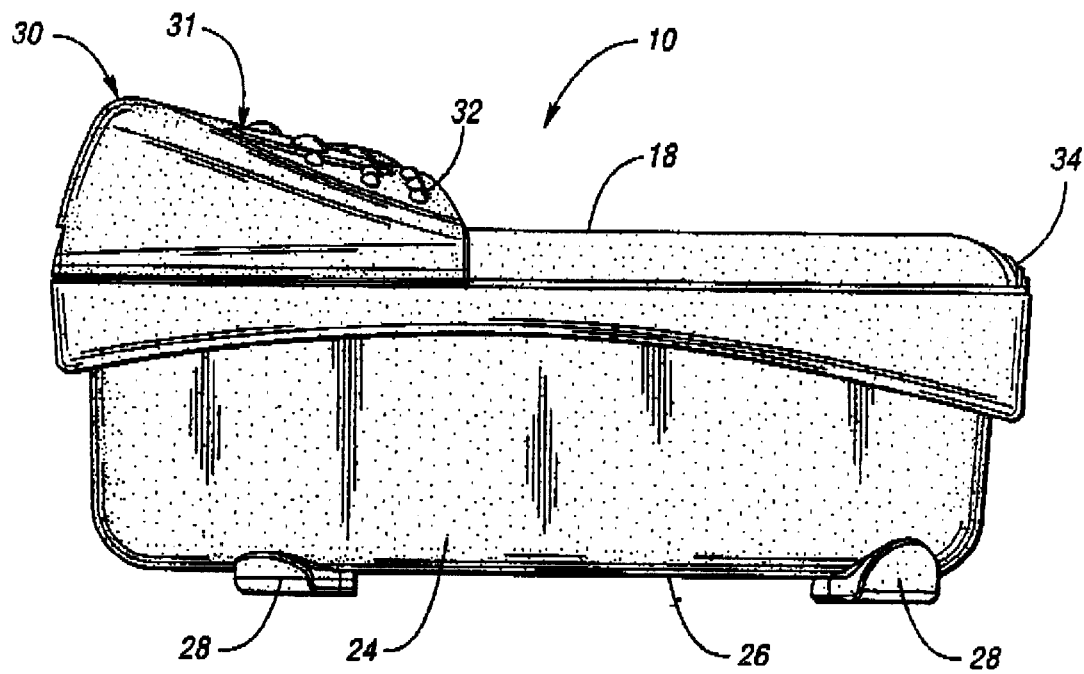
FIG. 4 is a side elevational view of the bath apparatus of FIG. 1.
Figure 5:
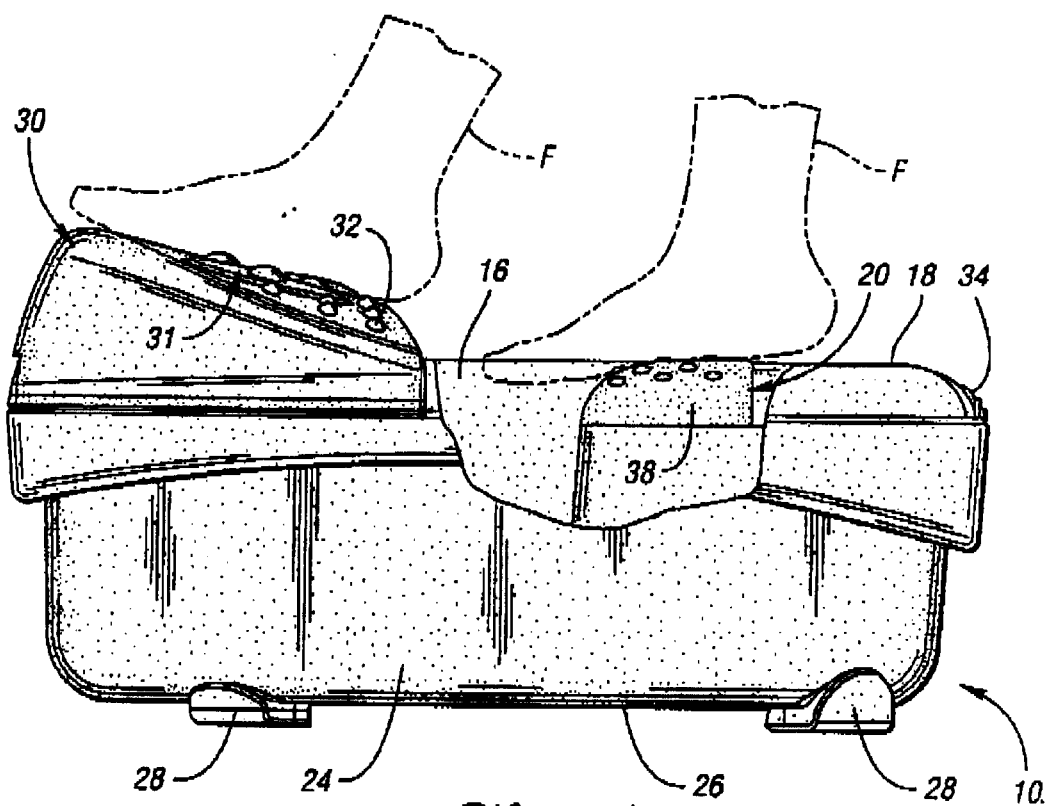
FIG. 5 is a side elevational view of the bath apparatus wherein the wall structure is partially cut away to show a user's feet engaging the infrared heating member and the hood therapy centers.

With reference to FIGS. 1 and 4, an outer housing 24 is provided to encase bath chamber 12, wherein outer housing 24 is spaced from bath chamber 12 to provide a location for housing the various mechanical/electrical assemblies of bath apparatus 10 described below with reference to FIG. 3. The base 26 of outer housing 24 is preferably provided with feet 28 constructed from a material such as rubber to prevent movement of bath apparatus 10 along a supporting surface.

Figure 14:
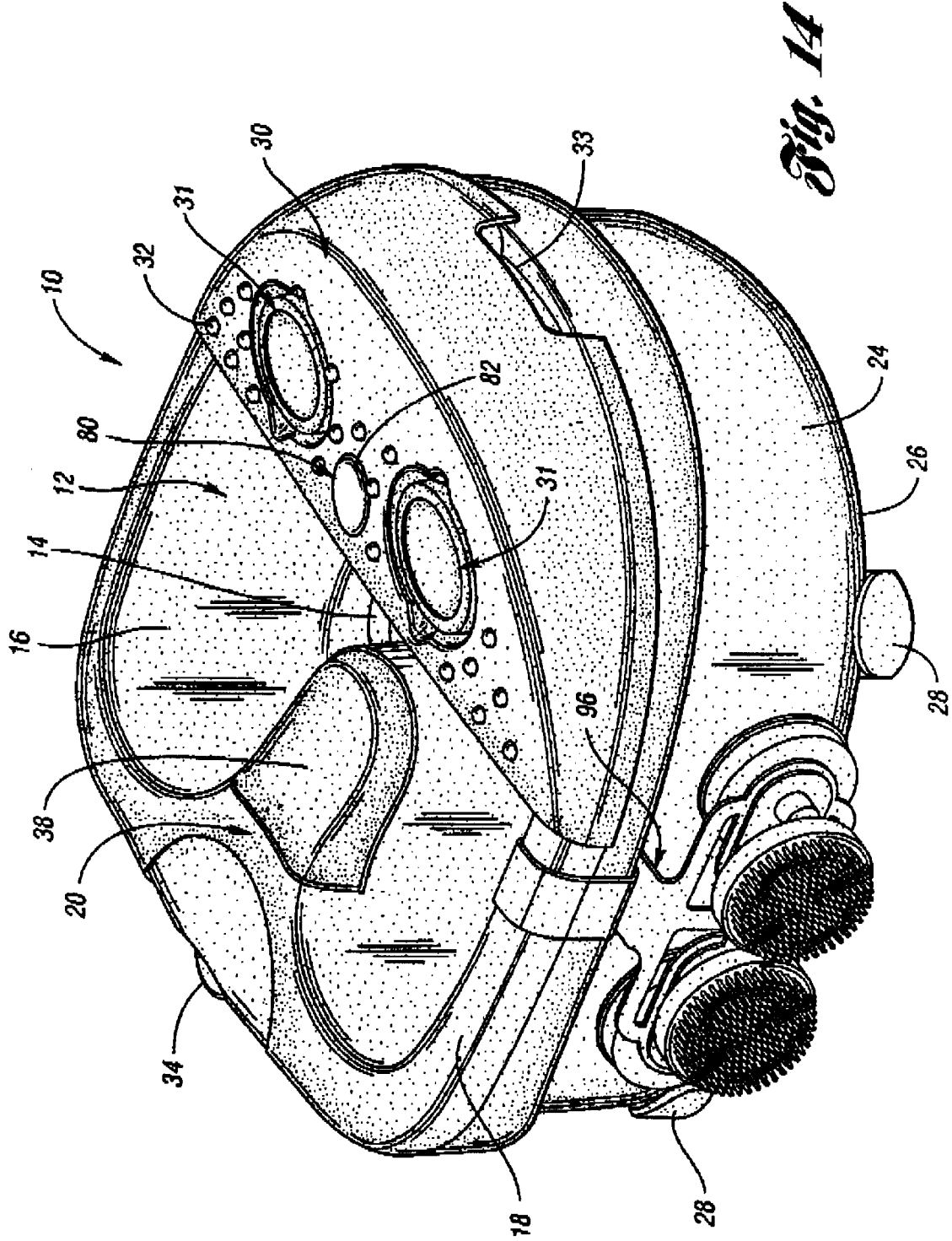
FIG. 14 is a perspective view of the bath apparatus according to the present invention showing a storage unit for the therapy attachments hanging from the wall structure.

As shown in FIGS. 1 and 2, bath apparatus 10 further includes a hood 30 adapted to be attached to wall structure 16 to at least partially cover bath chamber 12. Hood 30 is preferably constructed from a plastic material, and is sufficiently rigid so that it can be utilized to support one or both of a user's feet for providing targeted therapy. Specifically, hood 30 includes at least two spaced therapy centers 31 which allow for different types of therapy to be targeted to specific locations of the foot such as the ball, heel, or arch, and advantageously allow for both feet to receive therapy simultaneously. Therapy centers 31 are arranged to receive various rotatable therapy attachments, such as attachment 84 shown in FIGS. 1–2, wherein rotation of the therapy attachments is motorized, as described below with reference to FIGS. 6–8. In the embodiment shown herein, hood 30 is sloped upwardly away from the user at an angle of about 10 degrees from horizontal so as to be comfortable and ergonomic for the user to place his/her feet thereon, and includes raised nodes 32 similar to bottom surface nodes 22 to massage a user's feet upon contact. As best shown in FIG. 14, a hand slot 33 is provided on the back of hood 30 to facilitate carrying of bath apparatus 10.

For use, bath chamber 12 is filled with water such that a user, preferably seated, submerses his/her feet up to approximately the height of the ankles. A user can then easily remove his/her foot for placement on contact portion 20 or hood 30 for targeted therapy as described below. Of course, it is understood that contact portion 20 and hood 30 can have other locations on bath apparatus 10 which remain uncovered by water and are accessible to the user.

Referring again to FIGS. 1–2, a selector 34 is located on upper surface 18 of bath chamber 12, wherein selector 34 is rotatable by a user to selectively provide various combinations of heat, vibratory massage, and bubbles to the feet. Wiring interconnects selector 34 with each of the mechanical/electrical assemblies described below with reference to FIG. 3 which are powered via connection of a standard power cord 36 to any 110 V AC outlet. In a preferred embodiment, selector 34 can be set to provide three different combinations of bath functions: 1) vibratory massage, chamber heat, and targeted infrared heat; 2) vibratory massage, bubbles, chamber heat, and targeted infrared heat; and 3) bubbles and chamber heat. However, it is understood that other combinations of bath functions are fully contemplated in accordance with the present invention. Additionally, it is contemplated that selector 34 could be replaced by foot-activated, push-button controls.

With reference to FIGS. 1–3, several of the mechanical/electrical assemblies of bath apparatus 10 of the present invention will now be described. Each of the following assemblies is housed in the space between bath chamber 12 and outer housing 24 and is selectively powered as determined by the setting of selector 34. First, a heat therapy center in the form of heating member 38 is provided on contact portion 20 for providing heat to the foot surface when the foot F is placed on contact portion 20. Advantageously, heating member 38 provides the capability of focusing heat on the specific region of the foot desired by the user. According to a preferred embodiment of the present invention, heating member 38 uses infrared rays. Infrared rays allow heat to penetrate deep underneath the surface of the skin, causing the pores of the skin to be opened and promoting metabolism and excretion of the body through increased blood circulation. The applied pressure of the foot on heating member 38 can be adjusted by the user for optimum comfort. Heating member 38 preferably includes raised nodes 40 (FIGS. 1–2) to provide gently concentrated pressure to a user's foot. Of course, heating member 38 could alternatively be generally flat or could have any other contour suitable for contact with a user's foot.

In addition to heating member 38, a heater is provided in communication with bath chamber 12. As best shown in FIG. 3, the heater preferably includes a rope heating element 42 secured underneath bottom surface 14 of bath chamber 12. Upon receiving electrical power, as determined by selector 34, rope heating element 42 is operable to conduct heat to the water contained within bath chamber 12. The heated water maintained by rope heating element 42 relieves tired muscles and promotes circulation of the blood. Rope heating element 42 is positioned to wind back and forth to substantially cover bath chamber bottom surface 14. Rope heating element 42 preferably includes insulated conducting wires, wherein the conductive materials are capable of transmitting heat to bath chamber bottom surface 14 without generating temperatures that exceed the melting point of the plastic material used to construct bath apparatus 10. In addition to rope heating element 42, it is contemplated that a heater could be provided in communication with hood 30 to provide heat to a user's feet during targeted therapy as described below.

Bath apparatus 10 further includes a pump 44 disposed adjacent to bottom surface 14 of bath chamber 12 and in communication therewith. Pump 44 directs air into bath chamber 12 to generate air bubbles in the water contained therein. As shown in FIG. 3, pump 44 forces air through outlet tubes 46 which are connected to injection molded bubble egress tubes 48 formed in communication with bath chamber bottom surface 14. Air is forced out of a plurality of egress holes 50 (best shown in FIG. 2) that are provided along each bubble egress tube 48 to form air bubbles in the water contained in bath chamber 12. Of course, outlet tube 46 and egress tube 48 could be constructed as a single component. In a preferred embodiment, one egress tube 48 is disposed within first side 19 of bottom surface 14, and the other egress tube 48 is disposed within the second side 21 of bottom surface 14. Alternatively, a single egress tube 48 could be constructed to extend between and generally traverse both first and second sides 19, 21.

Bubble egress tubes 48 can be constructed to have various configurations which provide coverage of bath chamber bottom surface 14. In the example shown herein, bubble egress tubes 48 have a continuous curvilinear configuration. This configuration increases the capability for generating bubbles within a given area of bottom surface 14, and provides air bubbles in direct contact with a significant portion of the bathed body part. However, it is understood that other egress tube configurations in addition to the example illustrated herein are fully contemplated in accordance with the present invention.

In the embodiment depicted herein, bubble egress tubes 48 are disposed below bath chamber bottom surface 14, such that the plurality of egress holes 50 are generally flush with bottom surface 14. Alternatively, bubble egress tubes 48 could protrude at least partially above bottom surface 14, such that egress holes 50 would be raised above bottom surface 14 (not shown). In this alternative embodiment, the plurality of bubble egress holes 50 could be positioned at multiple axial locations along the egress tube 48, thereby providing an even greater ability to generate bubbles within a given area of bottom surface 14.

Figure 6:
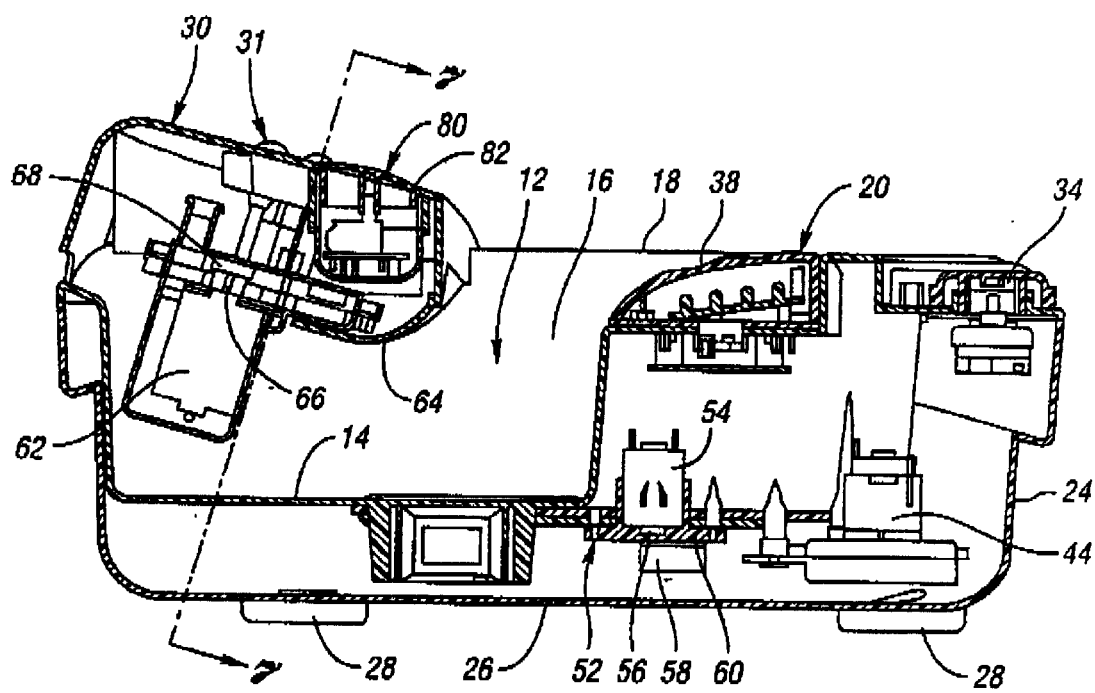
FIG. 6 is a cross-sectional view of the bath apparatus taken along line 6—6 of FIG. 2.

With reference to FIG. 3 and the cross-sectional view of FIG. 6, bath apparatus 10 further includes a vibration assembly 52 in communication with bath chamber 12 for imparting vibration to bath chamber 12 to provide a massaging effect to the feet. Vibration assembly 52 includes a motor 54 affixed to an underside of bath chamber 12, an output shaft 56 rotatably driven by motor 54, and a counterweight 58 affixed to output shaft 56. Vibration assembly 52 is affixed underneath a central portion of bath chamber 12 by a motor support bracket 60. When motor 54 is electrically powered, rotation of output shaft 56 and attached counterweight 58 imparts vibrations to motor support bracket 60, and these vibrations are then transferred to bath chamber 12 and the water contained therein in order to massage the feet. It is fully contemplated that variable vibration intensities could be provided in accordance with the present invention.

Figure 7:
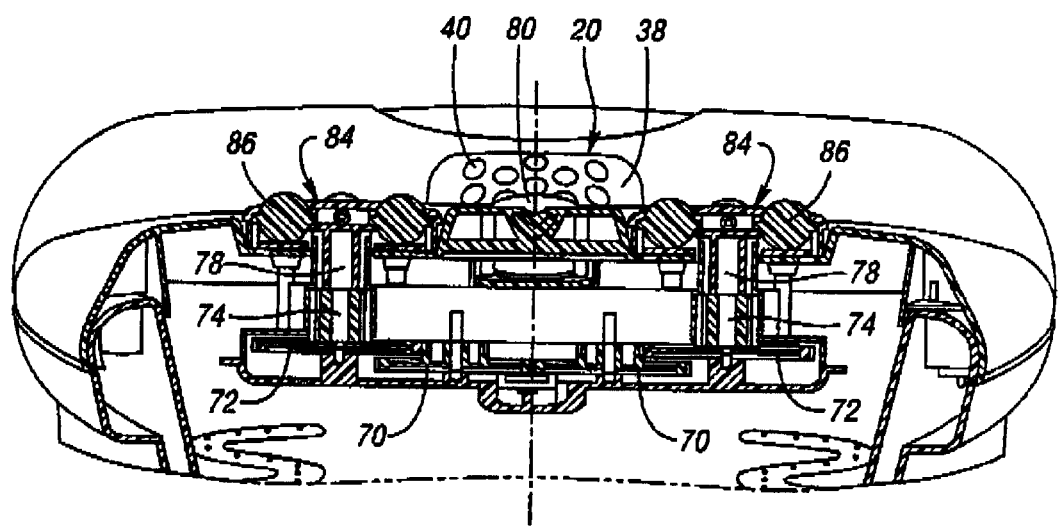
FIG. 7 is a cross-sectional view of the bath apparatus taken along line 7—7 of FIG. 6.
Figure 8A:
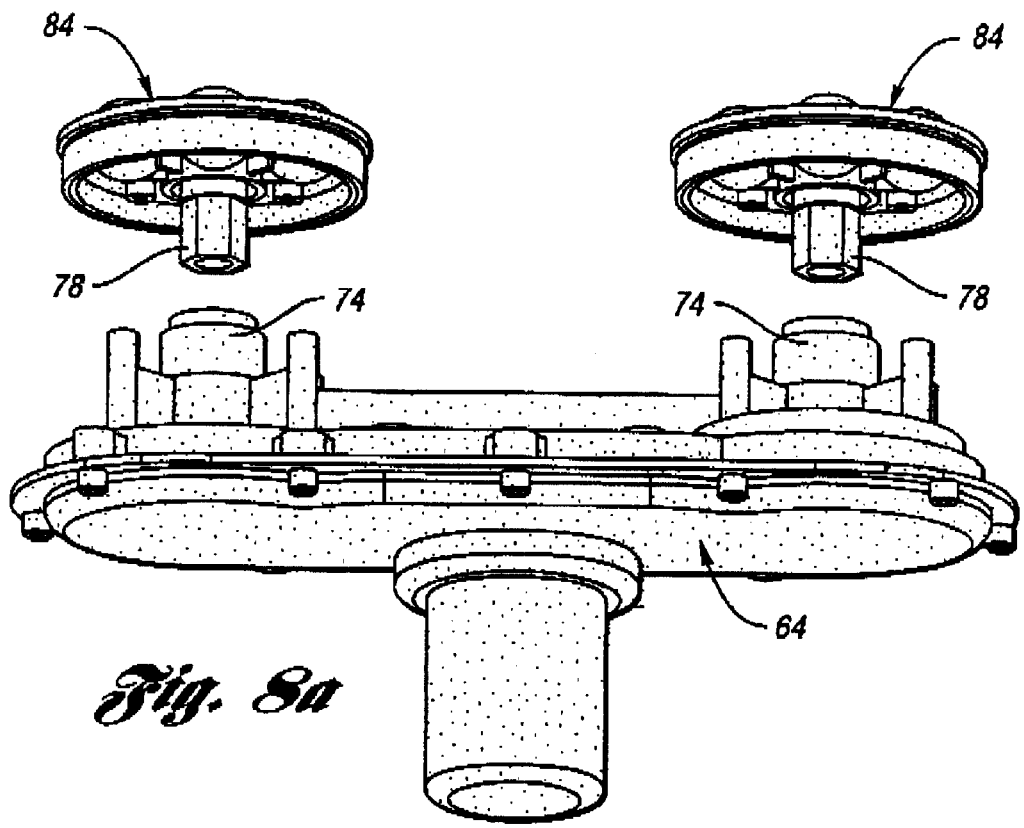
FIG. 8a is a fragmentary perspective view illustrating the motor and gear housing of the hood portion and the therapy attachments.
Figure 8B:
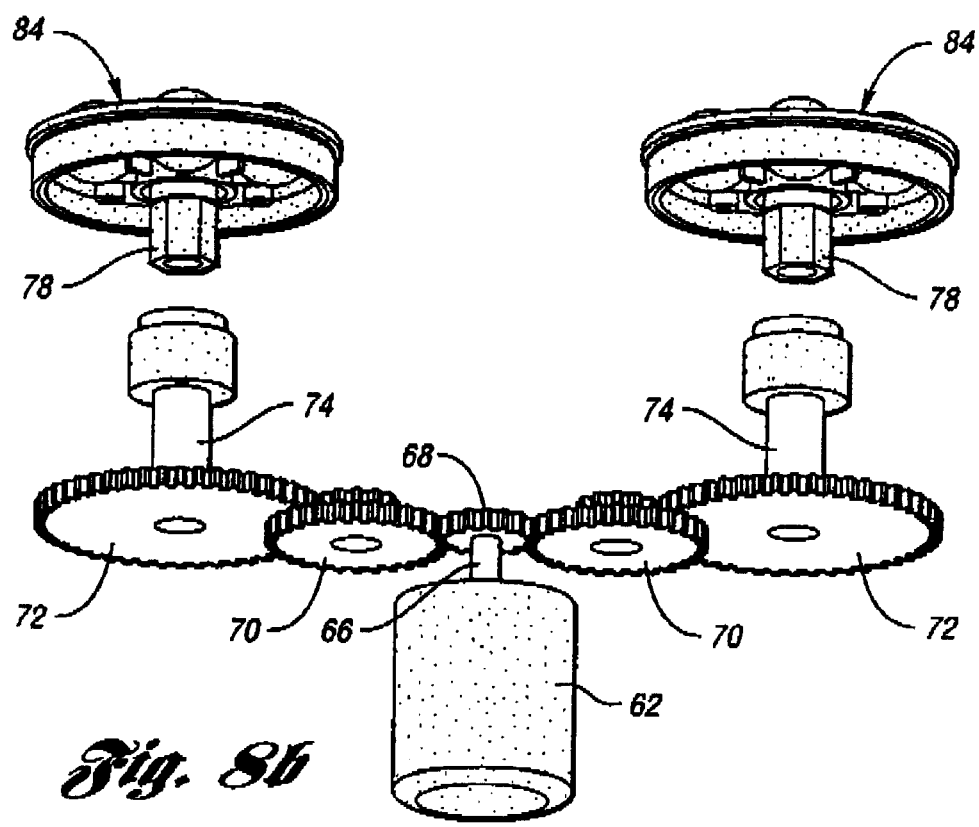

Turning now to the cross-sectional views of FIGS. 6–7 as well as the views of FIGS. 8a and 8b, the mechanical/ electrical assembly for operation of therapy centers 31 on hood 30 of bath apparatus 10 will now be described. A motor 62 is mounted on an underside of hood 30 and supported by housing 64. As best shown in FIG. 8*b*, motor 62 imparts rotary motion via a multi-stage gear train to therapy attachments, such as attachment 84, accessible on hood 30. Specifically, a motor output shaft 66 is rotatably driven by motor 62 and includes a first gear 68 affixed thereto. First gear 68 engages two intermediate gears 70 on either side thereof which are offset slightly forwardly of the axis of motor output shaft 66 toward the center of bath apparatus 10. Intermediate gears 70, in turn, engage outer gears 72 disposed outwardly thereof.

Figure 10:
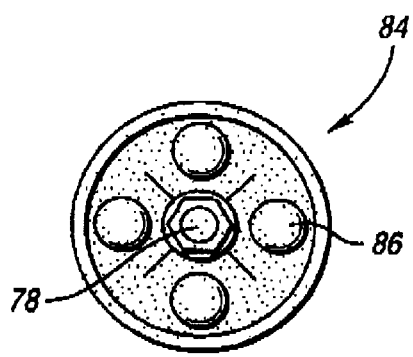
FIG. 10 is a bottom plan view of the first rotatable therapy attachment.
Figure 13A:
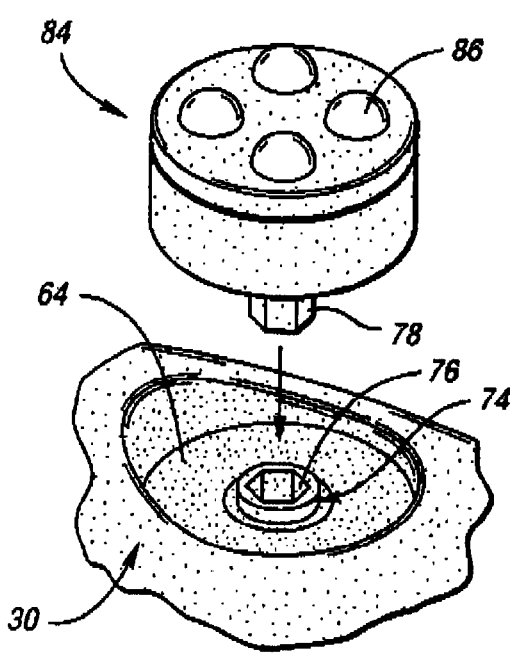
FIGS. 13a and 13b are fragmentary perspective views of the first rotatable therapy attachment before and after attachment to the receiving post accessible through the hood portion, respectively.
Figure 13B:
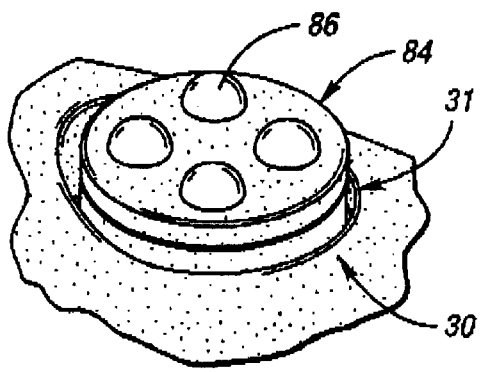

Each outer gear 72 includes a receiving post 74 affixed to and protruding upwardly therefrom. As best shown in FIG. 13*a*, each receiving post 74 extends through hood housing 64 to be accessible by the user and includes a recess 76 formed therein. Post recesses 76 are each configured to securely receive a corresponding projection 78 extending downwardly from therapy attachments 84, such that therapy attachments 84 will rotate with receiving posts 74 even when in contact with a user's foot F. In the example shown herein, both post recess 76 and attachment projection 78 (see FIG. 10) are hexagonal in shape. However, it is understood that recess 76 and projection 78 can have any other shape suitable for providing secure mating of posts 74 and therapy attachments 84 without slippage during rotation. Likewise, it is understood that post 74 could alternatively be received in a recess formed in attachment projection 78. When secured as shown in FIG. 13*b*, therapy attachments 84 preferably extend slightly above hood 30.

In a preferred embodiment, power is supplied to motor 62 via a standard push-push (push ON, push OFF) switch 80 accessible via hood 30. Switch 80 includes a flexible, preferably rubber, cover 82 which provides a waterproof design yet is flexible enough to allow for depression using a user's foot or toe. As an alternative to a push-push switch, switch 80 could be a multi-function switch in order to allow for multiple modes of activation, such as multiple rotation speeds of therapy attachments 84, with every press. As another option, the motorized rotation of therapy attachments 84 could be activated by pressure of the foot F applied thereon, which then would establish electrical contact to supply power to motor 62. In this case, the operation of motor 62 would not governed by switch 80, but rather power would be supplied to motor 62 as long as bath apparatus 10 was plugged in.

Figure 9:
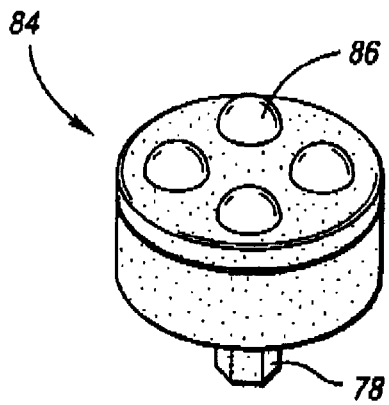
FIG. 9 is a perspective view of a first rotatable therapy attachment adapted to be received on the hood portion.
Figure 11:
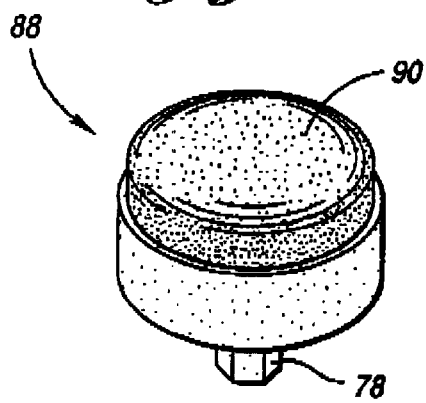
FIG. 11 is a perspective view of a second rotatable therapy attachment which includes a pumice stone.
Figure 12:
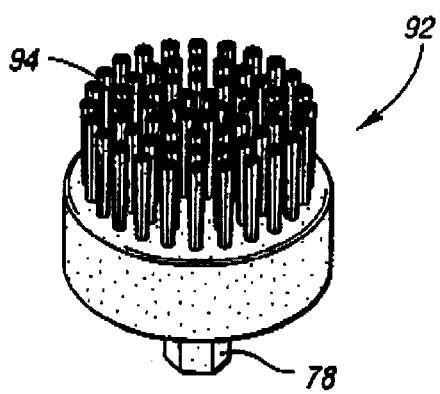
FIG. 12 is a perspective view of a third rotatable therapy attachment which includes a brush.

Turning now to FIGS. 9–12, several therapy attachments for use with bath apparatus 10 of the present invention are depicted, wherein the therapy attachments can be easily interchanged by a user. A first rotatable therapy attachment 84, as shown in FIG. 9, includes raised nodes 86 which provide pressure points to gently massage a user's foot F when contacted. FIG. 11 depicts a second rotatable therapy attachment 88 that includes a pumice stone 90 to smooth and soften skin on the soles of the feet, and FIG. 12 depicts a third rotatable therapy attachment 92 that includes a brush 94 to clean and exfoliate skin. In addition, a therapy attachment which includes a loofah (not shown) could be used. As shown in FIG. 14, a storage unit 96 is provided which is adapted to be attached to wall structure 16 for storing therapy attachments 84, 88, 92 therein when not in use. It is understood that the particular therapy attachments shown and described herein are merely exemplary, and that any other suitable therapy attachments can be used in accordance with the present invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for bathing a body part, the apparatus comprising:
   a bath chamber for containing a fluid and receiving the body part therein, the bath chamber including a bottom surface and a wall structure extending upwardly therefrom;
   a hood attached to the wall structure and arranged to at least partially cover the bath chamber;
   a motor mounted on an underside of the hood; and
   at least two spaced therapy centers disposed on the hood, the at least two therapy centers operably connected to the motor for providing therapy to the body part when the body part is placed on one of the at least two therapy centers.

2. The apparatus according to claim 1, wherein the at least two therapy centers are arranged to receive rotatable therapy attachments.

3. The apparatus according to claim 2, wherein the motor imparts rotary motion to the therapy attachments via a gear train.

4. The apparatus according to claim 3, wherein the gear train includes two outer gears each having a post affixed thereto, wherein the posts are accessible through a pair of openings in the hood.

5. The apparatus according to claim 4, wherein each therapy attachment includes a projection extending outwardly therefrom, and the attachment projection and the gear post are arranged to securely engage such that the therapy attachments will rotate with the gear posts even when in contact with the body part.

6. The apparatus according to claim 1, wherein hood includes a push-activated switch provided thereon for supplying power to the motor.

7. The apparatus according to claim 6, wherein the switch is a multi-function switch which allows for multiple modes of activation of the therapy centers.

8. The apparatus according to claim 6, wherein the switch is operable via depression by a user's foot.

9. The apparatus according to claim 2, wherein rotation of the therapy attachments is activated by pressure of the body part on each therapy attachment.

10. The apparatus according to claim 2, wherein the therapy attachments each include raised nodes.

11. The apparatus according to claim 2, wherein the therapy attachments each include a pumice stone.

12. The apparatus according to claim 2, wherein the therapy attachments each include a brush.

13. The apparatus according to claim 2, further including a storage unit adapted to be attached to the wall structure for storing the therapy attachments therein.

14. The apparatus according to claim 1, wherein the hood is sloped upwardly at an angle of about 10 degrees from horizontal.

15. The apparatus according to claim 1, wherein the hood includes raised nodes provided thereon.

16. The apparatus according to claim 1, wherein the hood includes a slot formed therein sized to accommodate a user's hand to facilitate carrying of the bath apparatus.

17. The apparatus according to claim 1, wherein the wall structure includes a contact area having a heating member disposed thereon for providing heat to the body part when the body part is placed on the heating member.

18. The apparatus according to claim 17, wherein the bath chamber is generally U-shaped and the contact area is generally peninsular and centrally disposed within the bath chamber, and the heating member is arranged to be uncovered by fluid contained in the bath chamber.

19. The apparatus according to claim 17, wherein the heating member uses infrared rays.

20. The apparatus according to claim 17, wherein the heating member includes raised nodes provided thereon.

21. The apparatus according to claim 1, further including a heater in communication with the bath chamber for maintaining the heat of the fluid contained therein, wherein the heater includes a rope heating element provided underneath the bottom surface of the bath chamber.

22. The apparatus according to claim 1, further including an air pump and at least one bubble egress tube in communication with the pump and the bath chamber bottom surface, the at least one bubble egress tube including a plurality of egress holes formed therein through which air from the pump is directed into the bath chamber in order to generate air bubbles in the fluid contained therein.

23. The apparatus according to claim 22, wherein the at least one bubble egress tube has a continuous curvilinear configuration.

24. The apparatus according to claim 1, further including a vibration assembly in communication with the bath chamber for imparting vibration to the bath chamber.

25. The apparatus according to claim 1, further including a plurality of raised nodes provided on the bottom surface of the bath chamber.

26. A bath apparatus, comprising:
   a bath chamber for containing water and receiving a user's feet therein, the bath chamber including a bottom surface and a wall structure extending upwardly therefrom;
   a hood attached to the wall structure, the hood arranged to at least partially cover the bath chamber;
   a motor mounted on an underside of the hood; and
   spaced therapy centers disposed on the hood which are arranged to receive rotatable therapy attachments, the therapy centers operably connected to the motor for imparting rotary motion to the therapy attachments such that, upon engagement by the feet, the therapy centers are capable of providing therapy to both feet simultaneously.

27. The bath apparatus according to claim 26, wherein the motor is operably connected to the therapy centers via a gear train.

28. The bath apparatus according to claim 27, wherein the gear train includes two outer gears each having a post affixed thereto, the posts extending through the hood to be accessible to the user, and wherein each therapy attachment includes a projection extending outwardly therefrom, the attachment projection and the gear post being arranged to securely engage such that the therapy attachments will rotate with the gear posts even when in contact with the body part.

29. The bath apparatus according to claim 26, wherein hood includes a push-activated switch provided thereon which is operable via depression by the user's feet for supplying power to the motor.

30. The bath apparatus according to claim 26, wherein the therapy attachments each include raised nodes.

31. The bath apparatus according to claim 26, wherein the therapy attachments each include a pumice stone.

32. The bath apparatus according to claim 26, wherein the therapy attachments each include a brush.

33. The bath apparatus according to claim 26, wherein the hood is sloped upwardly at an angle of about 10 degrees from horizontal.

34. The bath apparatus according to claim 26, wherein the bath chamber is generally U-shaped, and the wall structure includes a peninsular contact area having a heating member disposed thereon for providing heat to the body part when the body part is placed on the heating member.

35. The bath apparatus according to claim 26, further including a heater in communication with the bath chamber for maintaining the heat of the fluid contained therein, wherein the heater includes a rope heating element provided underneath the bottom surface of the bath chamber.

36. The bath apparatus according to claim 26, further including an air pump and at least one bubble egress tube in communication with the pump and the bath chamber bottom surface, the at least one bubble egress tube including a plurality of egress holes formed therein through which air from the pump is directed into the bath chamber in order to generate air bubbles in the fluid contained therein.

37. The bath apparatus according to claim 26, further including a vibration assembly in communication with the bath chamber for imparting vibration to the bath chamber.

38. A foot bath having multiple therapy centers, the foot bath comprising:
   a bath chamber for containing a fluid and receiving at least one foot therein, the bath chamber including a bottom surface and a wall structure extending upwardly therefrom, the wall structure having a contact area;
   a hood attached to the wall structure and arranged to at least partially cover the bath chamber;
   a heat therapy center disposed on the contact area for providing heat to the at least one foot when the at least one foot is placed on the heat therapy center; and
   spaced massage therapy centers disposed on the hood for providing massage to the at least one foot when the at least one foot is placed on one of the massage therapy centers.

* * * * *